US005700760A

United States Patent [19]

Magin et al.

[11] Patent Number: 5,700,760
[45] Date of Patent: Dec. 23, 1997

[54] HERBICIDAL AND PLANT GROWTH REGULANT COMPOSITIONS AND THEIR USE

[75] Inventors: Ralph W. Magin; Joe D. Sauer, both of Baton Rouge; Deborah A. Quebedeaux, Thibodaux, all of La.

[73] Assignee: Albemarle Corporation, Richmond, Va.

[21] Appl. No.: 627,853

[22] Filed: Apr. 3, 1996

[51] Int. Cl.$^6$ ..................................................... A01N 57/04
[52] U.S. Cl. ........................................... 504/206; 504/116
[58] Field of Search ..................................... 504/206, 116

[56] References Cited

U.S. PATENT DOCUMENTS

| | | | |
|---|---|---|---|
| 3,799,758 | 3/1974 | Franz | 504/206 |
| 4,075,002 | 2/1978 | Drewe et al. | 71/92 |
| 4,475,942 | 10/1984 | Bakel | 71/86 |
| 4,844,734 | 7/1989 | Iwasaki et al. | 71/120 |
| 5,258,359 | 11/1993 | Kassebaum et al. | 504/206 |
| 5,324,708 | 6/1994 | Moreno et al. | 504/206 |
| 5,464,806 | 11/1995 | Kassebaum et al. | 504/206 |

FOREIGN PATENT DOCUMENTS

| | | |
|---|---|---|
| 0274369 | 7/1988 | European Pat. Off. . |
| 0483095 | 4/1992 | European Pat. Off. . |
| 0498785 | 8/1992 | European Pat. Off. . |
| 0577914 | 1/1994 | European Pat. Off. . |
| 0617894 | 10/1994 | European Pat. Off. . |
| 9516351 | 6/1995 | WIPO . |

OTHER PUBLICATIONS

Wyrill, III, J. B. and Burnside, O. C. —"Glyphosate Toxicity to Common Milkweed and Hemp Dogbane as Influenced by Surfactants", Weed Science, vol. 25 Issue 3 (May), 1977, pp. 275–287.

*Primary Examiner*—José G. Dees
*Assistant Examiner*—Brian G. Bembenick
*Attorney, Agent, or Firm*—Philip M. Pippenger

[57] ABSTRACT

Glyphosate formulations which are effective even when employed at dosages below the dosage currently recommended for post-emergent herbicidal or plant growth regulant use are described. They are formulated as water solutions or as powders or granules of (a) one or more agriculturally acceptable amine, alkali metal, alkylsulfonium, alkylphosphonium, sulfonylamine, and/or aminoguanidine salts of glyphosate as the only herbicide or plant growth regulant used in forming said composition; and (b) a trihydrocarbyl amine oxide surfactant as the only surface active component used in forming said composition. The amine oxide is (i) a single alkyl dimethyl amine oxide in which the alkyl group is a linear alkyl group having in the range of 10 to 14 carbon atoms, or (ii) a combination of two alkyl dimethyl amine oxides of (i), or (iii) a combination of at least one alkyl dimethyl amine oxide in which the alkyl group is a linear alkyl group having in the range of 10 to 14 carbon atoms and at least one dialkyl methyl amine oxide in which the alkyl groups are linear alkyl groups each having in the range of 8 to 12 carbon atoms. Optionally, one or more agriculturally acceptable substances none of which is a herbicide, or a plant growth regulant or a surfactant can be included in the formulation.

41 Claims, No Drawings

HERBICIDAL AND PLANT GROWTH REGULANT COMPOSITIONS AND THEIR USE

TECHNICAL FIELD

This invention relates to glyphosate formulations which are highly effective even when employed at dosages below the dosage currently recommended for post-emergent herbicidal use against undesired vegetation.

BACKGROUND

Glyphosate, N-(phosphonomethyl)glycine, is a well-known widely used herbicide. It is generally employed in the form of an agriculturally acceptable salt.

In U.S. Pat. No. 5,116,401 to D. C. Young it is pointed out that although glyphosate, is a very active, broad spectrum, systemic, relatively environmentally safe herbicide, its solubility in water at 25° C. is only 1.2 weight percent and many of its homologs and salts are only slightly soluble or are essentially insoluble in water and organic solvents. Thus in practice, formulations of glyphosate salts with other components to enhance its solubility and its effectiveness are typically used.

Over the years a wide variety of substances, including surfactants, have been studied or proposed as adjuvants to enhance the effectiveness of glyphosate. For example, J. W. Kassebaum and H. C. Berk indicate in U.S. Pat. No. 5,317,003, that surfactants are usually employed to enhance the effectiveness of glyphosate when it is applied to the foliage of various plants, and that the most widely used surfactant in commercial compositions is an ethoxylated fatty amine. In addition, they refer to knowledge in the art that a particular surfactant used in an aqueous composition with a herbicide can enhance the effectiveness of the herbicide, whereas other surfactants have very little, if any, beneficial effect. They also note that some surfactants may exhibit antagonistic effects. As an example they cite the work of Wyrill and Burnside, *Weed Science, Volume* 25, (1977), pages 275–287 wherein, among other things, it was found that the surfactant ETHOQUAD 18/12 was relatively ineffective in enhancing phytotoxicity of glyphosate to hemp dogbane whereas in a separate experiment an analogous compound, ETHOQUAD 18/25, was one of the most effective surfactants tested.

Another similar finding of Wyrill and Burnside was that dimethyl cocoamine oxide (AROMOX DMCD) was less effective than dimethyl hexadecyl amine oxide in improving the phytotoxicity of glyphosate to hemp dogbane.

Despite the extensive studies and efforts devoted to improving the performance of glyphosate, a need exists for a way of potentiating the effectiveness of glyphosate salts such as the amine, sodium, alkylsulfonium, alkylphosphonium, sulfonylamine, and aminoguanidine salts thereof by means of an environmentally friendly aqueous formulation made from as few ingredients as possible, especially if this can be accomplished by use of readily available, cost-effective materials while at the same time avoiding the inclusion of polyvalent metal-containing and metalloid-containing components in the formulation.

This invention is deemed to fulfill this need in an effective and highly efficient manner.

THE INVENTION

This invention involves the discovery, inter alia, that despite the relative ineffectiveness of dimethyl cocoamine oxide in enhancing the effectiveness of glyphosate as compared to dimethyl hexadecyl amine oxide, certain linear alkyl dimethyl amine oxides with molecular weights lower than dimethyl hexadecyl amine oxide were even more effective than dimethyl hexadecyl amine oxide in increasing the phytotoxic effectiveness of glyphosate against a number of common plant species. This is surprising in light of the fact that the relatively ineffective dimethyl cocoamine oxide used by Wyrill and Burnside is a mixture of alkyl dimethyl amine oxides predominating in alkyl dimethyl amine oxides of molecular weights below that of dimethyl hexadecyl amine oxide.

Moreover, this invention makes it possible to achieve enhanced phytotoxic or plant growth regulant effectiveness in a formulation formed from as few as two active ingredients (glyphosate and amine oxide), both of which are readily available in the marketplace. Also, the particular amine oxides used are environmentally friendly and the formulation requires no polyvalent metal or metalloid components in its formation. Indeed the preferred compositions are devoid of metal and metalloid additive content, and most preferably contain only the elements C, H, O, N, P, and optionally S. Moreover, the liquid concentrates are most preferably formed using deionized water.

In accordance with one of its embodiments this invention provides a method of controlling vegetation by applying to plant foliage, preferably by spraying, a polyvalent metal-free and metalloid-free solution containing an effective herbicidal or plant growth regulant amount of a composition formed by intimately mixing the following ingredients with water: (a) at least one agriculturally acceptable amine, alkali metal, alkylsulfonium, alkylphosphonium, sulfonylamine, or aminoguanidine salt of glyphosate as the only herbicide used in forming the composition; and (b) a particular trihydrocarbyl amine oxide surfactant as the only surface active component used in forming the composition. The particular trihydrocarbyl amine oxide used in forming the composition is:

1) a single alkyl dimethyl amine oxide in which the alkyl group is a linear alkyl group having in the range of 10 to 14 carbon atoms, or 2) a combination of two alkyl dimethyl amine oxides of 1) above, or 3) a combination of at least one alkyl dimethyl amine oxide in which the alkyl group is a linear alkyl group having in the range of 10 to 14 carbon atoms, and at least one dialkyl methyl amine oxide in which the alkyl groups are linear alkyl groups each having in the range of 8 to 12 carbon atoms.

Another embodiment of this invention is a herbicide or plant growth regulant formulation which comprises a polyvalent metal-free and metalloid-free solution containing an effective herbicidal or plant growth regulant amount of a composition formed by intimately mixing the following ingredients with water:

(a) at least one agriculturally acceptable amine, alkali metal, alkylsulfonium, alkylphosphonium, sulfonylamine, or aminoguanidine salt of glyphosate as the only herbicide used in forming the composition;

(b) a trihydrocarbyl amine oxide surfactant as the only surface active component used in forming the composition, which trihydrocarbyl amine oxide is as set forth as 1), 2) and 3) above; and (c) optionally, one or more substances, that are not herbicides, or plant growth regulants, or surfactants, such as dyes, humectants, corrosion inhibitors, stickers, spreaders and thickeners.

Still another embodiment of this invention is a herbicide or plant growth regulant formulation which comprises a mixture in powder or granular form containing an effective herbicidal or plant growth regulant amount of a composition formed by intimately mixing together components (a) and (b) above, and optionally including one or more of (c) above. Such compositions can also be formed by evaporating to dryness (e.g., by spray drying, extrusion or pan granulation) a solution of components (a) and (b), and optionally (c) above. Application of the powder formulations to vegetation as foliar dusts for effecting control of the vegetation constitutes another embodiment of this invention.

It will be appreciated that to effect control of undesired plant vegetation pursuant to this invention, recourse may be had to herbicidal activity whereby undesired vegetation is killed and/or to plant growth regulant activity whereby the further growth of the vegetation is stunted, inhibited and/or slowed without actually killing all of the undesired vegetation treated with the composition.

The herbicidal (phytotoxic) and the growth regulant compositions include aqueous concentrates which can be shipped and stored until diluted with more water on site to produce the final solution for application to the foliage as by spraying. Likewise the herbicidal and the plant growth regulant compositions of this invention include the more dilute aqueous solutions for use in application to the foliage. These more dilute aqueous solutions are preferably formed simply by suitably diluting a concentrate of this invention with water (if a powder or granular concentrate) or with more water (if a liquid concentrate) to achieve the appropriate dosage, but alternatively, can be formed on site by intimately mixing the ingredients separately and/or in subcombinations with sufficient water on site to achieve the appropriate dosage. Use of the solid or liquid concentrates of this invention is preferable as it is a much simpler operation and minimizes the possibility of blending errors. Moreover, if desired, other components can be introduced into the final solution at the time the concentrate is blended with water to form the diluted solution for application to the foliage.

Of the particular amine oxides used in the practice of this invention, those of 1) above are preferred. The most preferred amine oxide ingredient is tetradecyl dimethyl amine oxide because of the great effectiveness which it has consistently exhibited in the test work conducted to date.

Component (a)

The identities and methods for the preparation of the glyphosate ingredient of the formulation are well known and are reported in the literature. See for example, U.S. Pat. No. 3,799,758 to J. E. Franz which describes amine salts and alkali metal salts of glyphosate, and the production of glyphosate by such methods as the phosphonomethylation of glycine, the reaction of ethyl glycinate with formaldehyde and diethylphosphite, and the oxidation of the corresponding aminophosphinic compounds. Another method involves conducting a Mannich reaction with phosphorous acid and formaldehyde on iminodiacetic acid followed by controlled oxidation to N-(phosphonomethyl)glycine. Typically the amine of the glyphosate amine salts has a molecular weight of less than 300. A preferred amine salt of glyphosate is a salt formed with isopropyl amine. Of the alkali metal salts of glyphosate, sodium is the preferred cation. Inasmuch as glyphosate has more than one replaceable hydrogen atom, either or both of mono- and dialkali metal salts of glyphosate can be formed and used. The alkylsulfonium salts of glyphosate are described for example in U.S. Pat. No. 4,315,765 to G. B. Large, and analogous procedures can be used for producing alkylphosphonium salts. Of the alkylsulfonium and alkylphosphonium salts, the trimethylsulfonium salt of glyphosate is preferred. Sulfonylamine and aminoguanidine salts of glyphosate which are also suitable for use pursuant to this invention are disclosed in EP-A-0 088 180. The patent literature contains numerous additional references to various other methods for the production of glyphosate. See for example U.S. Pat. Nos. 4,851,159; 4,898,972; 4,937,376; 4,952,723; 5,061,820; and 5,072,033 to Fields Jr. et al.; 5,023,369 to Fields, Jr.; 4,853,159 to Riley et. al; and 5,047,579 to Glowka et al., as well as relevant references cited in these patents. Fields, Jr. et al. U.S. Pat. No. 4,965,403 describes a process for producing the alkali metal salts of glyphosate. Aqueous solutions of glyphosate salts devoid of other adjuvants are commercially available from Monsanto Company and these solutions are suitable for use in forming the compositions of this invention.

Component (b)

Methods for producing the particular trialkyl amine oxides used in the practice of fills invention are also well known and are reported in the literature. Typically they involve the controlled oxidation of the appropriate trialkyl amine, such as with hydrogen peroxide. See for example U.S. Pat. Nos. 4,889,954; 4,942,260; 4,960,934; 4,970,340; 4,970,341; 4,994,614; 5,130,488; 5,208,374; and 5,254,735. Highly suitable compounds of types i) and 2) above and for use as in the combinations of type 3) above are available from Albemarle Corporation under the ADMOX trademark. Suitable dialkyl methyl amine oxides for use in the combinations of amine oxides of type 3) above are also available from Albemarle Corporation, in this case under the DAMOX trademark.

Table 1 sets forth general and preferred proportions for use in forming the liquid concentrate formulations of this invention. The percentages given in Table 1 are weight percentages, and represent weight percent of the total composition. The percentages for the amine, alkali metal, alkylsulfonium, alkylphosphonium, sulfonylamine, and/or aminoguanidine salt ("Glyphosate Salt") used in the practice of this invention as given in Table 1 are on an active ingredient basis and are in terms of glyphosate acid equivalent (i.e., the weight of the particular salt-forming portion of the product is excluded from the weight of the salt). Likewise the amount of any water associated with the salt as received is excluded from consideration as regards the percentages of the Glyphosate Salt shown in the table.

TABLE 1

| Ingredient | General Range, wt % | Preferred Range, wt % |
|---|---|---|
| (a) Glyphosate Salt | 0.1 to 65% | 18 to 65% |
| (b) Amine Oxide | 1 to 70% | 10 to 25% |
| Other Ingredient(s) | 0 to 20% | 0 to 5% |
| Water | Balance to 100% | Balance to 100% |

Table 2 sets forth the proportions which can be used in forming the powder or granular compositions of this invention. As in Table 1, the percentages given in Table 2 are weight percentages on an active ingredient basis, and represent weight percent of the total composition. And as above, the percentages for the amine, alkali metal, alkylsulfonium, alkylphosphonium, sulfonylamine, and/or aminoguanidine glyphosate salt ("Glyphosate Salt") used in the practice of this invention as given in Table 2 are in terms of glyphosate acid equivalent.

TABLE 2

| Ingredient | General Range, wt % | Preferred Range, wt % |
| --- | --- | --- |
| (a) Glyphosate Salt | 10 to 99% | 75 to 98% |
| (b) Amine oxide | 1 to 90% | 2 to 25% |
| Other Ingredient(s) | 0 to 20% | 0 to 10% |

The diluted solutions for application to the plant foliage are typically formed prior to application using a tank mixer, spray tank or similar apparatus. The dosage level of the composition applied to the plant foliage will depend to some extent upon the plant species being treated, and the prevailing weather conditions. Generally speaking, however, the amount applied will be a herbicidal or plant growth regulant amount falling within the range of about 50 to about 1250 grams of glyphosate (on an acid equivalent basis, i.e., excluding the weight of the cationic salt associated therewith) per hectare. In terms of ounces avoirdupois per acre this range corresponds (on the same acid equivalent basis) to about 0.7 to about 20 ounces of glyphosate per acre. In accordance with this invention it is preferred to employ a herbicidal or growth regulant amount (again on an acid equivalent basis) falling within the range of about 200 to about 830 grams of glyphosate per hectare which corresponds (on the same acid equivalent basis) to about 3 to about 12 ounces avoirdupois of glyphosate per acre, as this is generally sufficient to control most undesired plant species, is below the dosage currently recommended for herbicidal use of glyphosate formulations, and is thus more economical and environmentally friendly. On the basis of this disclosure and the new technology described herein, it is now possible to make departures from the foregoing ranges whenever such is deemed necessary or desirable in any given situation.

The following non-limiting Examples illustrate the practice and advantages of this invention.

EXAMPLE I

A field test was conducted in which the effectiveness of 4 compositions of this invention was directly compared to the effectiveness of dimethyl hexadecyl amine oxide, the more effective alkyl amine oxide as reported by Wyrill and Burnside, loc. cit. All solutions were at equal concentration of glyphosate isopropyl amine salt and equal concentrations of the respective surfactants were used. Each test formulation consisted of the aqueous solution made from the N-(phosphonomethyl)glycine isopropyl amine salt, water, and the surfactant under test. No other component or ingredient was employed in forming the test formulations. The glyphosate used in forming the test formulations was ROUND-UP® D-Pak from Monsanto, which is a 62.0% aqueous solution of the glyphosate isopropyl amine salt in water with no other component therein. The control formulation contained the commercial adjuvant INDUCE® (Helena Chemical Company) which, according to *A Guide to Agricultural Spray Adjuvants Used in the United States*, by T. L. Harvey, 1992–93 Edition, Thomson Publications, Fresno, Calif., page 33 is alkyl polyoxyalkane ether, free fatty acids and IPA, which is an adjuvant currently recommended for use in glyphosate formulations. The control formulation was applied at the recommended dosage level of 15 fluid ounces of glyphosate (active ingredient basis) per acre (624 grams of glyphosate per hectare). The amine oxide test formulations were applied at the dosage level of 10 fluid ounces of glyphosate per acre (416 grams of glyphosate per hectare, active ingredient basis), and thus provided only two-thirds of the active glyphosate herbicide as the control formulation. All solutions contained one percent of the particular adjuvant used.

All tests were conducted at the same experimental test site at the same time, and were performed with four replicate tests for each composition, using randomized plots. Each plot was 8 feet by 15 feet (2.4 meters by 4.6 meters) in size. Single applications were made between 9:30 a.m. and 11:30 a.m. on the same calm, sunny day with a relative humidity reading of 70% and an air/soil temperature of 89° F. and 88° F. (ca. 32° C. and ca. 31° C.), respectively. The application was made with a carbon dioxide pressurized back pack sprayer. The weed species populations were wild poinsettia (2–7 inches in height with 2–5 leaves per plant), and a combination of Johnson grass and barnyard grass (3–6 inches in height with 3–5 leaves per plant). The soil and leaf conditions were both dry at the time of application. Observations of percentage of control in the test plots were made 4 days, 7 days and 14 days after the application. No rainfall occurred in the first 24 hours after application. Thereafter the rainfall (in inches and in millimeters, respectively) was 0.11/2.79 in first three days after application, 0.06/1.52 in days 4 to 7, and 0.95/24.1 during week two after application.

Table 3 identifies the designations used in subsequent tables to identify test formulations employed. Table 4 summarizes the results obtained in the above tests on the wild poinsettia weed species. Table 5 gives the same information for the Johnson grass/barnyard grass species.

TABLE 3

Formulations Used in the Field Tests

| Formulations of the Invention | Composition |
| --- | --- |
| A | Glyphosate IPA salt (10 fluid oz./acre) in water to which was added 1 wt % n-decyl dimethyl amine oxide |
| B | Glyphosate IPA salt (10 fluid oz./acre) in water to which was added 1 wt % n-dodecyl dimethyl amine oxide |
| C | Glyphosate IPA salt (10 fluid oz./acre) in water to which was added 1 wt % n-tetradecyl dimethyl amine oxide |

TABLE 3-continued

Formulations Used in the Field Tests

| Formulations Not of the Invention | Composition |
|---|---|
| D | Glyphosate IPA salt (10 fluid oz./acre) in water to which was added 1 wt % n-hexadecyl dimethyl amine oxide |
| E | Glyphosate IPA salt (15 fluid oz./acre) in water to which was added 1 wt % INDUCE |

TABLE 4

Wild Poinsettia Control

| Formulation | % Control, 4 Days | % Control, 7 Days | % Control, 14 Days |
|---|---|---|---|
| A | 54 | 75 | 89 |
| B | 60 | 74 | 91 |
| C | 56 | 75 | 88 |
| E | 33 | 48 | 54 |
| F | 45 | 64 | 73 |

TABLE 5

Johnson Grass and Barnyard Grass Control

| Formulation | % Control, 4 Days | % Control, 7 Days | % Control, 14 Days |
|---|---|---|---|
| A | 53 | 75 | 81 |
| B | 61 | 71 | 80 |
| C | 48 | 68 | 73 |
| D | 31 | 48 | 46 |
| E | 59 | 76 | 84 |

EXAMPLE II

Another group of field tests was conducted in the same manner as in Example I except that the plant species treated was morning glory. Single applications were made on another day between 9:30 a.m. and 11:30 a.m. On the date of application the weather was calm, and sunny day with a relative humidity reading of 70% and an air/soil temperature of 85° F. and 88° F. (ca. 30° C. and ca. 31° C.), respectively. The morning glory populations were 3–7 inches in height with 3–6 leaves per plant). Observations of percentage control were made 3, 7 and 14 days after application. Rainfall during the test period (inches/millimeters) was none in the first 24 hours after application, 0.54/13.7 in the first 3 days, 1.32/33.5 in days 4–7, and 0.23/5.84 in the second week of the test. Otherwise, the conditions and operations were conducted in essentially the same manner as in Example I. Table 6 summarizes the results of these tests on morning glory, which is a known to be a troublesome species that is difficult for control by glyphosate.

TABLE 6

Morning Glory Control

| Formulation | % Control, 4 Days | % Control, 7 Days | % Control, 14 Days |
|---|---|---|---|
| A | 20 | 65 | 71 |
| B | 22 | 65 | 71 |
| C | 26 | 75 | 81 |
| D | 16 | 54 | 60 |
| E | 20 | 68 | 78 |

EXAMPLE III

Another group of field tests was conducted in the same manner as in Example I with the following exceptions:

a) Barnyard grass and crab grass; red weed; sickle pod; morning glory; and hemp sesbania were the plant species tested.

b) The tests were performed with three replicate tests for each composition, using randomized plots 10 feet by 15 feet (3.1 meters by 4.6 meters) in size.

c) Each amine oxide used (see Table 5) was employed in spray formulations in which the glyphosate concentrations were ⅓ and ⅔ of the recommended glyphosate concentration.

d) The applications were made between 10:00 am and 2:30 pm under weather conditions of 85°/92° F. (ca. 30°/33° C.) air/soil temperature, respectively, 75% relative humidity.

e) Observations of % control were made 7 days and 19 days after application.

f) In addition to formulations B and C, the compositions of the invention included the formulations set forth in Table 7.

TABLE 7

Formulations Used in the Field Tests

| Formulations of the Invention | Composition |
| --- | --- |
| K | Glyphosate IPA salt (5 fluid oz./acre) in water to which was added 1 wt % n-dodecyl dimethyl amine oxide |
| L | Glyphosate IPA salt (5 fluid oz./acre) in water to which was added 1 wt % n-tetradecyl dimethyl amine oxide |
| M | Glyphosate IPA salt (5 fluid oz./acre) in water to which were added 0.65 wt % n-dodecyl dimethyl amine oxide and 0.35 wt % n-tetradecyl dimethyl amine oxide |
| N | Glyphosate IPA salt (10 fluid oz./acre) in water to which were added 0.65 wt % n-dodecyl dimethyl amine oxide and 0.35 wt % n-tetradecyl dimethyl amine oxide |
| O | Glyphosate IPA salt (5 oz./acre) in water to which were added 0.5 wt % n-dodecyl dimethyl amine oxide and 0.5 wt % bis(n-decyl)methyl amine oxide |
| P | Glyphosate IPA salt (10 fluid oz./acre) in water to which were added 0.5 wt. % n-dodecyl dimethyl amine oxide and 0.5 wt % bis(n-decyl)methyl amine oxide |

Otherwise, the conditions and operations were conducted in essentially the same manner as in Example I. Tables 8–12 summarize the results of these tests on barnyard grass and crab grass; red weed; sickle pod; morning glory; and hemp sesbania, respectively. The dosages are in terms of fluid ounces of glyphosate (ROUNDUP D-PAK) per acre on an active ingredient basis.

TABLE 8

Barnyard Grass and Crab Grass Control

| Formulation | Dosage | % Control, 7 days | % Control, 19 days |
| --- | --- | --- | --- |
| K | 5 oz./acre | 82 | 80 |
| B | 10 oz./acre | 95 | 98 |
| L | 5 oz./acre | 87 | 60 |
| C | 10 oz./acre | 97 | 100 |
| M | 5 oz./acre | 83 | 85 |
| N | 10 oz./acre | 93 | 98 |
| O | 5 oz./acre | 57 | 50 |
| P | 10 oz./acre | 82 | 75 |
| E | 15 oz./acre | 93 | 92 |

TABLE 9

Red Weed Control

| Formulation | Dosage | % Control, 7 days | % Control, 19 days |
| --- | --- | --- | --- |
| K | 5 oz./acre | 58 | 75 |
| B | 10 oz./acre | 75 | 87 |
| L | 5 oz./acre | 57 | 68 |
| C | 10 oz./acre | 83 | 88 |
| M | 5 oz./acre | 48 | 60 |
| N | 10 oz./acre | 82 | 85 |
| O | 5 oz./acre | 45 | 75 |
| P | 10 oz./acre | 90 | 92 |
| E | 15 oz./acre | 93 | 92 |

TABLE 10

Sickle Pod Control

| Formulation | Dosage | % Control, 7 days | % Control, 19 days |
| --- | --- | --- | --- |
| K | 5 oz./acre | 30 | 80 |
| B | 10 oz./acre | 62 | 98 |
| L | 5 oz./acre | 33 | 60 |
| C | 10 oz./acre | 74 | 100 |
| M | 5 oz./acre | 55 | 85 |
| N | 10 oz./acre | 59 | 98 |
| O | 5 oz./acre | 33 | 50 |
| P | 10 oz./acre | 43 | 75 |
| E | 15 oz./acre | 62 | 70 |

TABLE 11

Morning Glory Control

| Formulation | Dosage | % Control, 7 days | % Control, 19 days |
| --- | --- | --- | --- |
| K | 5 oz./acre | 57 | 60 |
| B | 10 oz./acre | 70 | 77 |
| L | 5 oz./acre | 55 | 70 |
| C | 10 oz./acre | 78 | 88 |
| M | 5 oz./acre | 53 | 78 |
| N | 10 oz./acre | 68 | 77 |
| O | 5 oz./acre | 58 | 73 |
| P | 10 oz./acre | 75 | 82 |
| E | 15 oz./acre | 73 | 82 |

TABLE 12

Hemp Sesbania Control

| Formulation | Dosage | % Control, 7 days | % Control, 19 days |
| --- | --- | --- | --- |
| K | 5 oz./acre | 17 | 83 |
| B | 10 oz./acre | 18 | 90 |
| L | 5 oz./acre | 12 | 60 |
| C | 10 oz./acre | 35 | 80 |
| M | 5 oz./acre | 11 | 63 |
| N | 10 oz./acre | 20 | 78 |
| O | 5 oz./acre | 13 | 67 |
| P | 10 oz./acre | 28 | 82 |
| E | 15 oz./acre | 25 | 90 |

Optionally, one or more other suitable substances can be employed in the formulations of this invention provided no such substance materially detracts from the effectiveness of the composition in combatting the particular plant species to be controlled by use of the formulation. By "materially" in this context is meant that in tests conducted by concurrent application under identical conditions and using identical dosages of one or the other of two (2) test formulations to a plant species in three (3) identical pairs of test plots (each pair consisting of a Case I plot and a Case II plot) in the same substantially uniform test site, where in Case I the formulation of this invention does not contain such additional substance(s) whereas in Case II the identical formulation does additionally contain such additional substance(s), there is a reduction in the average percentages of the plant species controlled in the three (3) Case II plots as compared to the average percentages of the plant species controlled in the three (3) Case I plots, and the arithmetic difference between these averages exceeds 10%. Such other substances that may be used if they do not materially detract from the effectiveness of the composition include dyes, pigments, humectants, corrosion inhibitors, thickeners, adhering agents (stickers), spreading agents, and like materials. Such other substances can be introduced into the formulation in any sequence relative to components (a) and (b) hereof, i.e., such materials can be added before, after or at the same time as either or both of components (a) and (b). In this connection, it will be recalled that the one or more glyphosate salts constitute(s) the only herbicide(s) or plant growth regulant(s) used in forming the compositions of this invention. Likewise one or more of the herein-described amine oxides constitute(s) the only surfactant(s) used in forming the compositions of this invention. This ensures that the substantial benefits provided by this invention are realized in full.

The powder or granular formulations of this invention may be mixed with a finely-divided solid diluent such as talc, gypsum, Fuller's earth, kaolin, kieselguhr, bentonite, dolomite, calcium carbonate, and powdered magnesia. They may also be formulated as dispersible powders or grains, and in this case it is desirable to include a wetting agent to facilitate the dispersion of powder or grains in the liquid carrier. Additionally, formulations in the form of powders can be applied to vegetation as foliar dusts.

It is to be understood that the terms "ingredient" or "component" or "substance" as used anywhere in the specification or claims hereof, whether used in the singular or plural, are used in the sense that it is a substance employed in forming the powder or granular concentrate or aqueous solution, and thus at least prior to mixing with other ingredients, components and/or addition to an aqueous medium, the ingredient or component is in the chemical form specified. It matters not what chemical changes, transformations and/or reactions, if any, take place in the mixture or aqueous medium itself as such changes, transformations and/or reactions are the natural result of bringing the specified ingredients or components together as solids or in an aqueous medium.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A method of controlling vegetation which comprises applying to plant foliage a polyvalent metal-free and metalloid-free solution containing a herbicidal or plant growth regulant amount of a composition formed by intimately mixing the following ingredients with water:
    a) at least one agriculturally acceptable mine, alkali metal, alkylsulfonium, alkylphosphonium, sulfonylamine, or aminoguanidine salt of glyphosate as the only herbicide used in forming said composition; and
    b) a trihydrocarbyl mine oxide surfactant as the only surface active component used in forming said composition, said trihydrocarbyl amine oxide being selected from the group consisting of (i) a single alkyl dimethyl mine oxide in which said alkyl group is a linear alkyl group having in the range of 10 to 14 carbon atoms, (ii) a combination of two alkyl dimethyl amine oxides of (i), and (iii) a combination of at least one alkyl dimethyl amine oxide in which said alkyl group is a linear alkyl group having in the range of 10 to 14 carbon atoms and at least one dialkyl methyl mine oxide in which said alkyl groups are linear alkyl groups each having in the range of 8 to 12 carbon atoms.

2. A method according to claim 1 wherein ingredient a) is an amine or alkylsulfonium salt of glyphosate.

3. A method according to claim 1 wherein ingredient a) is the isopropyl amine salt of glyphosate.

4. A method according to claim 1 wherein ingredient b) is a single linear alkyl dimethyl amine oxide in which the linear alkyl group has an even number of carbon atoms.

5. A method according to claim 1 wherein ingredient b) is n-tetradecyl dimethyl amine oxide.

6. A method according to claim 1 wherein ingredient b) is a combination of n-dodecyl dimethyl amine oxide and n-tetradecyl dimethyl amine oxide.

7. A method according to claim 1 wherein ingredient b) is a combination of n-dodecyl dimethyl amine oxide and bis(n-decyl) methyl amine oxide.

8. A method according to claim 1 wherein ingredient a) is the isopropyl amine salt of glyphosate and wherein ingredient b) is a single linear alkyl dimethyl amine oxide in which the linear alkyl group has an even number of carbon atoms.

9. A method according to claim 1 wherein ingredient a) is the isopropyl amine salt of glyphosate and wherein ingredient b) is n-tetradecyl dimethyl amine oxide.

10. A method according to claim 1 wherein ingredient a) is the isopropyl amine salt of glyphosate and wherein ingredient b) is a combination of n-dodecyl dimethyl amine oxide and n-tetradecyl dimethyl amine oxide.

11. A method according to claim 1 wherein ingredient a) is the isopropyl amine salt of glyphosate and wherein ingredient b) is a combination of n-dodecyl dimethyl amine oxide and bis(n-decyl) methyl amine oxide.

12. A herbicide or plant growth regulant formulation which comprises a polyvalent metal-free and metalloid-free solution containing a herbicidal or plant growth regulant amount of a composition formed by intimately mixing the following ingredients with water:
    a) at least one agriculturally acceptable amine, alkali metal, alkylsulfonium, alkylphosphonium, sulfonylamine, or aminoguanidine salt of glyphosate as the only herbicide or plant growth regulant used in forming said composition;
    b) a trihydrocarbyl amine oxide surfactant as the only surface active component used in forming said composition, said trihydrocarbyl amine oxide being selected from the group consisting of (i) a single alkyl dimethyl amine oxide in which said alkyl group is a linear alkyl group having in the range of 10 to 14 carbon atoms, (ii) a combination of two alkyl dimethyl amine oxides of (i), and (iii) a combination of at least one alkyl dimethyl amine oxide in which said alkyl group is a linear alkyl group having in the range of 10 to 14 carbon atoms and at least one dialkyl methyl amine oxide in which said alkyl groups are linear alkyl groups each having in the range of 8 to 12 carbon atoms; and c) optionally, one or more agriculturally acceptable substances none of which is a herbicide, or a plant growth regulant or a surfactant.

13. A formulation according to claim 12 wherein ingredient a) is an amine or alkylsulfonium salt of glyphosate.

14. A formulation according to claim 12 wherein ingredient a) is the isopropyl amine salt of glyphosate.

15. A formulation according to claim 12 wherein ingredient b) is a single linear alkyl dimethyl amine oxide in which the linear alkyl group has an even number of carbon atoms.

16. A formulation according to claim 12 wherein ingredient b) is n-tetradecyl dimethyl amine oxide.

17. A formulation according to claim 12 wherein ingredient b) is a combination of n-dodecyl dimethyl amine oxide and n-tetradecyl dimethyl amine oxide.

18. A formulation according to claim 12 wherein ingredient b) is a combination of n-dodecyl dimethyl amine oxide and bis(n-decyl) methyl amine oxide.

19. A formulation according to claim 12 wherein ingredient a) is the isopropyl amine salt of glyphosate and wherein ingredient b) is a single linear alkyl dimethyl amine oxide in which the linear alkyl group has an even number of carbon atoms.

20. A formulation according to claim 12 wherein ingredient a) is the isopropyl amine salt of glyphosate and wherein ingredient b) is n-tetradecyl dimethyl amine oxide.

21. A formulation according to claim 12 wherein ingredient a) is the isopropyl amine salt of glyphosate and wherein ingredient b) is a combination of n-dodecyl dimethyl amine oxide and n-tetradecyl dimethyl amine oxide.

22. A formulation according to claim 12 wherein ingredient a) is the isopropyl amine salt of glyphosate and wherein ingredient b) is a combination of n-dodecyl dimethyl amine oxide and bis(n-decyl) methyl amine oxide.

23. A formulation according to claim 12 consisting of the solution resulting from intimately mixing ingredients a) and b) with water.

24. A herbicide or plant growth regulant formulation which comprises a polyvalent metal-free and metalloid-free powder or granular mixture containing a herbicidal or plant growth regulant amount of a composition formed by intimately mixing together the following ingredients:

a) at least one agriculturally acceptable amine, alkali metal, alkylsulfonium, alkylphosphonium, sulfonylamine, or aminoguanidine salt of glyphosate as the only herbicide or plant growth regulant used in forming said composition;

b) a trihydrocarbyl amine oxide surfactant as the only surface active component used in forming said composition, said trihydrocarbyl amine oxide being selected from the group consisting of (i) a single alkyl dimethyl amine oxide in which said alkyl group is a linear alkyl group having in the range of 10 to 14 carbon atoms, (ii) a combination of two alkyl dimethyl amine oxides of (i), and (iii) a combination of at least one alkyl dimethyl amine oxide in which said alkyl group is a linear alkyl group having in the range of 10 to 14 carbon atoms and at least one dialkyl methyl amine oxide in which said alkyl groups are linear alkyl groups each having in the range of 8 to 12 carbon atoms; and c) optionally, one or more agriculturally acceptable substances none of which is a herbicide, or a plant growth regulant or a surfactant.

25. A formulation according to claim 24 wherein ingredient a) is an amine or alkylsulfonium salt of glyphosate.

26. A formulation according to claim 24 wherein ingredient a) is the isopropyl amine salt of glyphosate.

27. A formulation according to claim 24 wherein ingredient b) is a single linear alkyl dimethyl amine oxide in which the linear alkyl group has an even number of carbon atoms.

28. A formulation according to claim 24 wherein ingredient b) is n-tetradecyl dimethyl amine oxide.

29. A formulation according to claim 24 wherein ingredient b) is a combination of n-dodecyl dimethyl amine oxide and n-tetradecyl dimethyl amine oxide.

30. A formulation according to claim 24 wherein ingredient b) is a combination of n-octyl dimethyl amine oxide and bis(n-decyl) methyl amine oxide.

31. A formulation according to claim 24 wherein ingredient a) is the isopropyl amine salt of glyphosate and wherein ingredient b) is a single linear alkyl dimethyl amine oxide in which the linear alkyl group has an even number of carbon atoms.

32. A formulation according to claim 24 wherein ingredient a) is the isopropyl amine salt of glyphosate and wherein ingredient b) is n-tetradecyl dimethyl amine oxide.

33. A formulation according to claim 24 wherein ingredient a) is the isopropyl amine salt of glyphosate and wherein ingredient b) is a combination of n-dodecyl dimethyl amine oxide and n-tetradecyl dimethyl amine oxide.

34. A formulation according to claim 24 wherein ingredient a) is the isopropyl amine salt of glyphosate and wherein ingredient b) is a combination of n-octyl dimethyl amine oxide and bis(n-decyl) methyl amine oxide.

35. A formulation according to claim 24 formed by spray drying a water solution formed by mixing ingredients a) and b) with water.

36. A method of controlling vegetation which comprises applying to plant foliage a herbicidal or plant growth regulant amount of a polyvalent metal-free and metalloid-free herbicide or plant growth regulant composition formed by intimately mixing together the following ingredients:

a) at least one agriculturally acceptable amine, alkali metal, alkylsulfonium, alkylphosphonium, sulfonylamine, or aminoguanidine salt of glyphosate as the only herbicide or plant growth regulant used in forming said composition;

b) a trihydrocarbyl amine oxide surfactant as the only surface active component used in forming said composition, said trihydrocarbyl amine oxide being selected from the group consisting of (i) a single alkyl dimethyl amine oxide in which said alkyl group is a linear alkyl group having in the range of 10 to 14 carbon atoms, (ii) a combination of two alkyl dimethyl amine oxides of (i), and (iii) a combination of at least one alkyl dimethyl amine oxide in which said alkyl group is a linear alkyl group having in the range of 10 to 14 carbon atoms and at least one dialkyl methyl amine oxide in which said alkyl groups are linear alkyl groups each having in the range of 8 to 12 carbon atoms; and c) optionally, one or more agriculturally acceptable substances none of which is a herbicide, or a plant growth regulant or a surfactant.

37. A method according to claim 36 wherein said herbicide or plant growth regulant composition is in the form of a powder, and wherein said composition is applied to the foliage as a foliar dust.

38. A method according to claim 1 wherein said ingredients consist of a) and b).

39. A formulation according to claim 12 wherein said ingredients consist of a) and b).

40. A formulation according to claim 24 wherein said ingredients consist of a) and b).

41. A method according to claim 36 wherein said ingredients consist of a) and b).

* * * * *